United States Patent [19]

Motai et al.

[11] Patent Number: 4,797,358

[45] Date of Patent: Jan. 10, 1989

[54] MICROORGANISM OR ENZYME IMMOBILIZATION WITH A MIXTURE OF ALGINATE AND SILICA SOL

[75] Inventors: Hiroshi Motai; Yaichi Fukushima; Katsumichi Osaki, all of Noda; Katutoshi Okamura, Nagoya; Kazutaka Imai, Owariasahi, all of Japan

[73] Assignees: Kikkoman Corporation, Noda; Fuji-Davison Chemical, Ltd., Aichi, both of Japan

[21] Appl. No.: 738,181

[22] Filed: May 28, 1985

[51] Int. Cl.$^4$ .................. C12N 11/14; C12N 11/02; C12N 11/10; C12N 11/04

[52] U.S. Cl. ..................... 435/176; 435/177; 435/178; 435/180; 435/181; 435/182

[58] Field of Search ............... 435/174, 177, 176, 178, 435/180, 181, 182

[56] References Cited

U.S. PATENT DOCUMENTS

| | | | |
|---|---|---|---|
| 3,766,013 | 10/1973 | Forgione et al. | 435/182 |
| 4,148,689 | 4/1979 | Hino et al. | 435/176 |
| 4,272,617 | 6/1981 | Kaetsu et al. | 435/182 |
| 4,659,664 | 4/1987 | Butz | 435/176 |

FOREIGN PATENT DOCUMENTS

| | | |
|---|---|---|
| 120190 | 4/1977 | Japan. |
| 49392 | 1/1979 | Japan. |
| 1267685 | 7/1972 | United Kingdom. |

OTHER PUBLICATIONS

Birnbaum et al., Immobilized Cells, Solid Phase Bichemistry, John Wiley & Sons, N.Y., 1983, pp. 679&706–708.

Zaborsky O., Immobilized Enzymes, CRC Press, Cleveland, Ohio, 1973, pp. 70–74, 78 & 79.

R. K. Iler, The Chemistry of Silica, John Wiley & Sons, 1979, pp. 379–381.

Primary Examiner—David M. Naff
Attorney, Agent, or Firm—Banner, Birch, McKie & Beckett

[57] ABSTRACT

A microorganism or enzyme is mixed with an alginate and a silica sol in the presence of water to obtain a liquid mixture having a pH of 3 to 10 and containing an alginate concentration of 0.5 to 3.5% (w/v) and a silica concentration originating from the silica sol of 0.5 to 35% (w/v). The mixture is contacted with a gelling agent in the form of an aqueous solution to obtain a gel containing the microorganism or enzyme.

8 Claims, No Drawings

MICROORGANISM OR ENZYME IMMOBILIZATION WITH A MIXTURE OF ALGINATE AND SILICA SOL

BACKGROUND OF THE INVENTION

1. Field of the Invention

This invention relates to a process for preparing an immobilized microorganism or enzyme. More particularly, the invention relates to a process for preparing an immobilized microorganism or enzyme by using a mixture of an alginate and silica sol as an entrapping material.

2. Description of the Prior Art

An immobilizing method of microorganisms or enzymes by entrapping them with an alginate is known. This method causes little reduction of enzyme activity in the course of immobilizing operation as no heating is required and the gelation can be effected under the relatively mild conditions. This method is also safe in terms of food sanitation, and attempts are being made of the application of this technique to the food and pharmaceutical industries.

However, the alginate matrix gel is weak in mechanical strength and liable to deform and swell in comparison with the gel entrapped by using a polymeric compound such as acrylamide or polymethacrylate, so that great difficulties are involved in use of such alginate matrix gel as a packed bed type reactor which is generally used in the fermentation processes.

Methods are also known in which an inorganic substance, especially silica gel is used as immobilizing carrier for the gel containing a microorganism or enzyme. For instance, British Pat. No. 1,267,685 discloses a method in which hydrochloric acid is added to an aqueous solution of sodium silicate to prepare a silica sol having a pH of 1.6, then this sol is dialyzed to remove sodium chloride to obtain a stabilized silica sol, and after adjusting the pH to around 5-8, it is added with a microorganism or an enzyme and is converted to gel In the methods disclosed in Japanese Patent Application Kokai (Laid-Open) Nos. 120190/77 and 49392/79, an enzyme is adsorbed on colloidal silica, followed by the gelation thereof by the addition of a salt such as magnesium chloride, sodium carbonate or the like, and then the gel is subjected to freezing and thawing to obtain an pulverized immobilized gel.

These methods, however, had the following problems: much time is required for the preparation of silica sol used as base; the entrapping and immobilizing (gelation) operations are complicated; in use of these gels as a bioreactor, since such gels are an irregular or pulverized silica gel, no satisfactory packing effect is obtained when such gels are packed in a substrate reaction vessel, unless the gels are shaped into a form suited for said vessel In order to eliminate these defects of the prior arts the present inventors have made more extensive studies and found that, when immobilizing a microorganism or enzyme, the use of a mixture of silica sol and an alginate as entrapping material enables prompt gelation with an ordinary gelling agent such as calcium chloride, aluminum chloride or the like, that the thus obtained gel containing the microorganism or the enzyme is extremely high in mechanical strength and has also strong resistance against the swelling because of a dual gel matrix structure comparising alginate gel and silica gel, and that, in the course of the immobilizing process, there takes place little reduction of enzyme activity. The present invention was achieved on the basis of these findings.

SUMMARY OF THE INVENTION

The object of the present invention is to provide a process for preparing an immobilized microorganism or enzyme without causing any substantial reduction of enzyme activity while maintaining high mechanical gel strength by a simple operation with high efficiency.

According to this invention, there is provided a process for preparing an immobilized microorganism or enzyme which comprises mixing a microorganism or an enzyme with an alginate and silica sol in the presence of water to obtain a liquid mixture having a pH of 3 to 10, and contacting said mixture with a gelling agent which is in the form of an aqueous solution.

DETAILED DESCRIPTION OF THE INVENTION

The invention will be described in more detail below.

The microorganism used in the present invention may be any species of microorganism such as bacteria, yeasts, molds, ray fungi, etc. Also, the enzymes of every variety can be used in this invention, the typical examples thereof are oxidoreductases such as alcohol dehydrogenase, glucose oxidase, lactic acid dehydrogenase, etc.; transferases such as D-glutamyl transferase, glutamine transaminase, hexokinase, etc.; lyases such as fumarase, aspartase, β-tyrosinase, etc.; isomerases such as glucose isomerase, mannose isomerase, etc; and ligases such as glutathione synthetase, NAD synthetase, etc.

Said enzymes may be used after the insolubilizing treatment with tannin or a multifunctional crosslinking reagent, or after the adsorption treatment on an insoluble carrier.

For insolubilizing an enzyme with tannin, the enzyme is added with a solution containing tannin in an amount of 1 to 10 times (w/w) the amount of the enzyme and reacted under stirring at pH of 8 or below, preferably 3 to 7, and the produced precipitate is separated by using a usual separating means such as centrifugation or filtration to obtain the insolubilized enzyme.

As tannin, one may use tannic acid, pyrogallol tannin such as nutgalls-tannin or Chinese gallotannin, and catechol tannin such as tanniferous substance (catechol polymer) extracted from tea, cacao and the like. Such tannin used in this invention may not be refined provided that it has the required tannic action, and for instance commercially sold tannin of persimmon can be used. Also, said tannin substances can be used either singly or as a mixture of two or more of them For insolubilizing an enzyme with a multifunctional crosslinking agent, the enzyme is added to the aqueous solution containing 1 to 20% (w/v) of a multifunctional crosslinking agent and is reacted at 5°-40° C. for 10 munutes to 16 hours, and the produced precipitate is separated by using a usual separating means such as centrifugation, filtration, etc., to obtain an insolubilized enzyme.

Polyaldehydes, isocyanates and the like are suited for use as the multifunctional crosslinking agent in this invention. Typical examples are dialdehyde starch glyoxal, malonaldehyde, succinic aldehyde, glutaraldehyde, pimelic dialdehyde, hexamethylene isocyanate, p-toluylene diisocyante and the like. Glutaraldehyde is most preferred.

For the adsorption treatment of the enzyme on an insoluble carrier, the following methods are available: an insoluble carrier, for example, ordinary adsorbents such as active carbon, silica gel, acid clay, porous glass, etc., or ion exchangers such as DEAE-Sephadex, CM-Sephadex, DEAE-cellulose, CM-cellulose, Amberlite IR-45, Dowex-50, etc., are packed in a column and an aqueous solution of said enzyme is passed therethrough, or said insoluble carrier is mixed with the enzyme solution and the mixture is stirred to give the enzyme adsorbed on said carrier, said mixture being, if necessary, further subjected to a separating treatment such as centrifugation or filtration to separate the liquid portion, thereby obtaining the enzyme adsorbed on said insoluble carrier. If necessary, said enzyme-adsorbed insoluble carrier may be further added and reacted with said multifunctional crosslinking agent.

Said microorganism, enzyme, enzyme insolubilized with tannin or a multifunctional crosslinking agent, or enzyme absorbed on an insoluble carrier can be used as it is or after suspending them in water, a buffer solution or a hydrophilic organic solvent.

As the buffer solution used in the above-mentioned treatment, there can be employed, for example, acetate buffer solution, McIlvaine's buffer solution, phosphate buffer solution, tris buffer solution, Veronal buffer solution and the like. Methyl alcohol, ethyl alcohol, propyl alcohol, acetone and the like can be used as the hydrophilic organic solvent in said treatment. The concentration of such organic solvent in an aqueous solution used in the treatment is usually about 10 to 20% (w/v).

Then said microorganism, enzyme, enzyme insolubilized with tannin or a multifunctional crosslinking agent or enzyme adsorbed on an insoluble carrier, or a suspension thereof in water, a buffer solution or a hydrophilic organic solvent is mixed with an alginate or an aqueous solution thereof and silica sol used as a entrapping material to obtain a liquid mixture having a pH of 3 to 10, preferaby 6 to 8. In the preparation of said liquid mixture, said microorganism or enzyme, which may have been treated as mentioned above, may be first added to an alginate or an aqueous solution thereof, followed by the addition thereto of silica sol and mixing of the materials; or said microorganism or enzyme may be first added to silica sol, followed by the addition of an alginate or an aqueous solution thereof; or may be added to both of an alginate or an aqueous solution thereof and silica sol simultaneously, followed by mixing.

Addition of an alginate or an aqueous solution thereof and silica sol is preferably made in such a manner that the final content of alginate in the mixture is 0.5–3.5% (w/v) and the final $SiO_2$ concentration originating from the silica sol is 0.5–35% (w/v).

Examples of alginates usable as entrapping material in this invention include sodium alginate, potassium alginate, ammonium alginate and the like. As silica sol, its property is that particle diameter of silica colloid is 1 nm to 100 nm, the solvent is water, and pH is 2 to 11, there can be used, for example, a product obtained by adding a mineral acid such as hydrochloric acid, nitric acid, sulfuric acid, etc., to an aqueous solution of an alkali silicate such as sodium silicate, then desalting the mixed solution by the dialysis and adjusting the pH, or a product obtained by passing an aqueous solution of an alkali silicate through an ion exchange resin to exchange the cation in the solution. Preferred examples of such silica sol are, for example, Snowtex-20, Snowtex-30 and Snowtex-40 (all being the products by Nissan Chemical Co., Ltd., $SiO_2$ content being adjusted to 20 to 40%).

Then the above-mentioned mixture with a pH of 3–10 is added dropwise into a gelling agent in the state of an aqueous solution under stirring by using a fine-orifice nozzle (for example, a syringelike injector), a porous plate or other suitable means, or said mixture is sprayed as atomized particles on and contacted with the gelling agent by using an atomizer, preferably a pressure atomizer, to obtain an immobilized microorganism or enzyme.

As the gelling agent, there can be used, for example, calcium chloride, aluminum chloride, calcium acetate, aluminum sulfate and the like in the form of a usually about 1–10% (w/v) aqueous solution.

In case the mixture is added dropwise into the liquid gelling agent under stirring as the above-mentioned gelling means, the resulting immobilized gel of microorganism or enzyme has an average particle size of 1 to 5 mm, and in case said mixture is atomized and conatacted with the gelling agent, there can be obtained the fixed gel substantially uniform in particle size, with the average particle size not exceeding 800–900 microns. The more uniform and the smaller tme particle size is, the higher the efficiency of reaction with the substrate becomes.

The immobilized microorganism or enzyme obtained according to this invention is very high in mechanical gel strength, not swell easily because of a dual gel matrix structure and is extremely limited in the decrease of enzyme activity in the course of the treatment. Thus, the process of this invention is of great industrial significance.

The present invention will be described in more detail below by way of the embodiments thereof, but the invention is not limited thereto.

EXAMPLE 1

200 ml of a nutrient medium (pH 5.0) containing 2% (w/v) of glucose, 1% (w/v) of peptone and 1% (w/v) of yeast extract was placed in a 1-liter flask and, after sterilization in the usual way, inoculated with Saccharomyces cerevisiae IFO 0224, which was then cultured at 30° C. for 48 hours. 20 ml of the resulting culture solution ($10^9$ cells/ml) was added to a mixed solution consisting of 100 ml of Snowtex-40 (produced by Nissan Chemical Co., Ltd.) adjusted to pH 7.0 by adding a hydrochloric acid aqueous solution and 100 ml of a 3% (w/v) aqueous solution of sodium alginate (produced by Wako Pure Chemical Co., Ltd.), followed by mixing [pH of the mixture: 7.0; $SiO_2$ concentration: 18.0% (w/v); sodium alginate concentration: 1.36% (w/v)]. The mixture was added dropwise into a 5% (w/v) solution of calcium chloride under stirring by using a syringe (orifice diameter: 2 mm; inner diameter: 20 mm) to obtain a globular immobilized yeast (hereinafter referred to as immobilized yeast of Example 1).

As control, 20 ml of said yeast culture solution ($10^9$ cells/ml) was added to and mixed with 200 ml of a 1.5% (w/v) aqueous solution of sodium alginate [pH of the mixture: 7.0; sodium alginate concentration: 1.36% (w/v)], and the mixture was added dropwise into a 5% (w/v) solution of calcium chloride by using the same syringe as mentioned above to obtain a control globular immobilized yeast.

The alcohol productivity was determined by filling 65 g of said immobilized yeast in a jacketed column (inner diameter: 3 cm; height: 15 cm) maintained at 30°

C., passing a liquid medium (pH 3.3) containing 10% (w/v) of glucose, 0.1% (w/v) of yeast extract and 0.2% (w/v) of ammonium sulfate through said column for 20 days continuously by using the ascending method (SV=0.15) to effect alcohol fermentation, and measuring the alcohol concentration of the fermentation solution. The results are shown in Table 1.

TABLE 1

| Alcohol concentration (v/v) | Sample | |
|---|---|---|
| | Control | Immobilized yeast of Example 1 |
| 10th day | 4.04 | 4.62 |
| 20th day | 4.47 | 4.70 |

As seen from Table 1, the immobilized yeast of Example 1 had very excellent alcohol fermentability in comparison with the control, notwithstanding the long-time retention. Also, the gel of the immobilized yeast of Example 1 was small in the degree of swelling, with the coefficient of expansion of the gel in the course of fermentation being only 130% as compared with 185% of the control.

EXAMPLE 2

100 ml of a solution formed by dissolving urease (Type IX, produced by Sigma Corp.) in a 0.05M phosphate buffer solution was added to a mixed solution of 100 ml of a 2% (w/v) aqueous solution of sodium alginate and 100 ml of a silica sol (Snowtex-30 of Nissan Chemical Co., Ltd.) adjusted to a pH 8.0 by adding a hydrochloric acid aqueous solution and mixed [pH of the mixture: 8.0; $SiO_2$ concentration: 14.3% (w/v); sodium alginate concentration: 0.95% (w/v)], and the resulting mixture was sprayed by pressure onto a 5% (w/v) solution of calcium chloride by Wagner Handy Painter W-170 (two-fluid type; nozzle orifice diameter: 0.7 mm, mfd. by Japan Wagner Spraytex Co., Ltd.) under a spray pressure of 120 kg/$cm^2$ G to obtain an immobilized urease (average particle diameter: 350 microns).

EXAMPLE 3

10 g of a leucine aminopeptidase preparation obtained from a bran culture of Aspergillus oryzae FERM P-1149 by subjecting it to ammonium sulfate fractionation and further purifying the fraction with DEAE-cellulose was dissolved in a 0.05M tris buffer solution (pH 7.0), and the resulting mixed solution was mixed with a solution of 20 g of tannic acid (produced by Wako Pure Chemical) in 200 ml of 0.05M tris buffer solution (pH 7.0) and centrifuged in the usual way to obtain an insolubilized enzyme. To this insolubilized enzyme was added 20 ml of a 0.05M tris buffer solution (pH 7.0) to prepare an insolubilized enzyme liquid.

Said insolubilized enzyme liquid was added to a mixed solution of 100 ml of a 4% (w/v) aqueous solution of sodium alginate and 80 ml of a silica sol (Snowtex-20 of Nissan Chemical Co., Ltd.) adjusted to a pH 6.0 by adding a hydrochloric acid aqueous solution, followed by mixing [pH of the mixture: 6.0; $SiO_2$ concentration: 8.0% (w/v); sodium alginate concentration: 2.0% (w/v)], and the resulting mixture was added dropwise into a 5% (w/v) solution of calcium chloride under stirring by using the same syringe as used in Example 1 to obtain a globular immobilized enzyme [leucine aminopeptidase activity: 25,000 units/gel (0.8 g)].

The enzyme activity of leucine aminopeptidase was determined according to the Nakadai's method [Tadanobu Nakadai: Nippon Shoyu Kenkyūjo Zasshi, 3, 99 (1977)] by using leucine-p-nitroanilide as substrate.

EXAMPLE 4

800 ml of a liquid medium (pH 7.2) containing 12% (w/v) of sodium chloride, 3% (w/v) of glucose, 1% (w/v) of meat extract, 1% (w/v) of yeast extract, 0.1% (w/v) of sodium thioglycolate and 0.58% (w/v) of acetic acid was put into a 1-liter flask and, after sterilization in the usual way, inoculated with Pediococcus halophilus FERM P-6420, the medium was then cultured at 30° C. for 24 hours. The resulting culture solution was centrifuged in the usual way and concentrated to 20-fold. 10 ml of this concentrated solution ($2 \times 10^{10}$ cells/ml) was added to and mixed with a mixed solution consisting of 100 ml of a 3% (w/v) aqueous solution of sodium alginate and 50 ml of a silica sol (Snowtex-40 of Nissan Chemical Co., Ltd.) adjusted to a pH of 7.0 by adding a hydrochloric acid aqueous solution [pH of the mixture: 7.0; $SiO_2$ concentration: 12.5% (w/v); sodium alginate concentration: 1.9% (w/v)], and the resulting mixture was added dropwise into a 5% (w/v) solution of calcium chloride under stirring by using the same syringe as used in Example 1 to obtain a globular immobilized lactic acid bacteria.

70 g of said immobilized lactic acid bacteria was packed into a jacketed column (inner diameter: 3 cm; height: 15 cm) maintained at 30° C., and a liquid medium (pH 7.2) containing 1% (w/v) of meat extract, 1% (w/v) of polypeptone, 1% (w/v) of yeast extract, 1% (w/v) of glucose, 0.1% (w/v) of sodium thioglycolate and 15% (w/v) of common salt was passed through said column for a total period of 30 days by using the ascending method (SV=0.1) to effect lactic acid fermentation. The results are shown in Table 2.

TABLE 2

| | 1st day | 5th day | 10th day | 15th day | 25th day | 30th day |
|---|---|---|---|---|---|---|
| Lactic acid concentration % (w/v) | 0.36 | 0.78 | 0.78 | 0.78 | 0.80 | 0.82 |

As seen from Table 2, the immobilized lactic acid bacteria obtained in Example 4 had a very excellent lactic acid fermentability not-withstanding the long-time retention.

What is claimed is:

1. A process for preparing an immobilized microorganism or enzyme which comprises mixing a starting microorganism or enzyme in the presence of water with an alginate selected from the group consisting of sodium alginate, potassium alginate and ammonium alignate and a silica sol, said silica sol havig a silica colloid particle diameter in the range of from 1 nm to 100 nm, a water solvent, and a pH in the range of 2 to 11, to obtain a liquid mixture having a pH of 3 to 10and containing an alginate concentration of 0.5 to 3.5% (w/v) and a silica concentration originating from the silica sol of 0.5 to 35% (w/v) selected from the group consisting of calcium chloride, aluminum chloride, calcium acetate and aluminum sulfate in the form of an aqueous solution to gel the mixture.

2. The process of claim 1, wherein the starting microorganism is a bacterium, yeast or mold.

3. The process of claim 1, wherein the enzyme is selected from the group consisting of enzymes insolubilized with tannin or a multi-functional cross-linking agent, enzymes adsorbed on an insoluble carrier, and enzymes suspended in water, a buffer solution or a hydrophlic organic solvent.

4. The process of claim 3, wherein the tannin is tannic acid or pyrogallol tannin.

5. The process of claim 3, wherein the multi-functional cross-linking agent is a polyaldehyde or an isocyanate.

6. The process of claim 3, wherein the insoluble carrier is activated carbon, silica gel, acid clay, porous glass or an ion exchanger.

7. The process of claim 1, wherein the contact of the liquid mixture with the gelling agent is conducted by adding the liquid mixture dropwise into the gelling agent under stirring or by spraying the mixture on the gelling agent.

8. Immobilized microorganisms or enzymes obtained according to the process of claim 1.

UNITED STATES PATENT AND TRADEMARK OFFICE
CERTIFICATE OF CORRECTION

PATENT NO. : 4,797,358
DATED : January 10, 1989
INVENTOR(S) : Hiroshi Motai et al.

It is certified that error appears in the above-identified patent and that said Letters Patent is hereby corrected as shown below:

Col. 4, line 45, "109" should read --$10^9$--.

Claim 1, line 12 (Col. 6, line 61), after "(w/v)", insert --and contacting the mixture with a gelling agent--.

Signed and Sealed this

Eleventh Day of July, 1989

Attest:

DONALD J. QUIGG

Attesting Officer

Commissioner of Patents and Trademarks